(12) United States Patent
Mo et al.

(10) Patent No.: US 11,305,091 B2
(45) Date of Patent: Apr. 19, 2022

(54) CIRCADIAN RHYTHM MANAGEMENT APPARATUS AND SYSTEM

(71) Applicant: KOOKMIN UNIVERSITY INDUSTRY ACADEMY COOPERATION FOUNDATION, Seoul (KR)

(72) Inventors: Hyun Sun Mo, Seoul (KR); Young Rag Do, Seoul (KR); Dae Jeong Kim, Seoul (KR); Dae Hwan Kim, Seoul (KR); Sung Yeon Jang, Seoul (KR); In Hwan Jung, Seoul (KR); Dong Myung Kim, Seoul (KR); Seong Jin Choi, Seoul (KR); Sanggyu Yim, Seoul (KR); Hyung Min Kim, Seoul (KR); Sun Woong Choi, Seoul (KR); Gu Min Jeong, Seoul (KR); Seung Min Lee, Seoul (KR)

(73) Assignee: KOOKMIN UNIVERSITY INDUSTRY ACADEMY COOPERATION FOUNDATION, Seoul (KR)

(*) Notice: Subject to any disclaimer, the term of this patent is extended or adjusted under 35 U.S.C. 154(b) by 177 days.

(21) Appl. No.: 16/525,183

(22) Filed: Jul. 29, 2019

(65) Prior Publication Data
US 2020/0230346 A1    Jul. 23, 2020

(30) Foreign Application Priority Data

Jan. 23, 2019   (KR) .......................... 10-2019-0008822

(51) Int. Cl.
*A61M 21/02* (2006.01)
*A61M 21/00* (2006.01)

(52) U.S. Cl.
CPC ...... *A61M 21/02* (2013.01); *A61M 2021/0044* (2013.01); *A61M 2205/3306* (2013.01);
(Continued)

(58) Field of Classification Search
CPC ...... A61M 21/00–02; A61M 2205/587; A61M 2205/3306; H05B 33/08; A61B 5/4836;
(Continued)

(56) References Cited

U.S. PATENT DOCUMENTS

| | | | | |
|---|---|---|---|---|
| 2001/0056293 A1* | 12/2001 | Brainard | .................. | A61N 5/06 607/88 |
| 2018/0339127 A1* | 11/2018 | Van Reen | ............ | A61N 5/0618 |
| 2019/0336789 A1* | 11/2019 | Garner | .................. | H05B 45/20 |

FOREIGN PATENT DOCUMENTS

KR     1020010090519     10/2001

OTHER PUBLICATIONS

Oh et al., "Healthy, natural, efficient and tunable lighting: four-package white LEDs for optimizing the circadian effect, color quality, and vision performance," Light Sci. Appl., 3, e141, 2014. (Year: 2014).*

* cited by examiner

*Primary Examiner* — Thaddeus B Cox
(74) *Attorney, Agent, or Firm* — K&L Gates LLP

(57) ABSTRACT

Disclosed are an apparatus and a system for managing circadian rhythm. The apparatus includes an illuminance measuring portion which measures a bio illuminance value of external light using a circadian lambda filter which passes the external light along according to a circadian rhythm sensitivity curve and a visual lambda filter which passes the external light along according to a visual sensitivity curve, a controller which outputs a control signal for reinforcing a user's circadian rhythm on the basis of the bio illuminance value, and a circadian rhythm reinforcing portion which
(Continued)

emits light of a circadian wavelength band toward the user according to the control signal.

14 Claims, 7 Drawing Sheets

(52) U.S. Cl.
CPC ..... *A61M 2230/04* (2013.01); *A61M 2230/06* (2013.01); *A61M 2230/50* (2013.01)
(58) Field of Classification Search
CPC .......... A61B 5/4857; A61N 2005/0626; A61N 2005/0662
See application file for complete search history.

FIGs.

CIRCADIAN RHYTHM MANAGEMENT APPARATUS AND SYSTEM

CROSS-REFERENCE TO RELATED APPLICATION

This application claims priority to and the benefit of Korean Patent Application No. 2019-0008822, filed on Jan. 23, 2019, the disclosure of which is incorporated herein by reference in its entirety.

BACKGROUND

1. Field of the Invention

The present invention relates to an apparatus and a system for managing rhythm, and more particularly, to an apparatus and a system for managing circadian rhythm that is capable of diagnosing circadian rhythm of a user by calculating a more precise bio-illuminance value and strengthening the circadian rhythm of the user according to a diagnosis result.

2. Discussion of Related Art

A human being lives having a cycle of a single day, which is referred to as circadian rhythm. The circadian rhythm is most influenced by light.

On the basis of the sun, a variety of living things have altered and adapted together according to a daily change of the sun in which it becomes increasingly brighter as the sun rises in the morning and it becomes increasingly darker as the sun sets in the evening. Also, human beings have lived with a cycle of a single day while being influenced by a daily cycle of the sun, by getting up as the sun rises to start the day and taking a rest and sleeping as the sun sets.

Meanwhile, when light is received in the evening time period, a secretion of melatonin, which is one hormone having a great effect on sleep of our bodies, is suppressed such that sound sleep is disturbed and a probability of being exposed to a variety of diseases is increased.

Diseases caused by disturbance of circadian rhythm include seasonal affective disorder, somnipathy, depression, fatigue caused by time difference, health conditions related to shift work, and the like. To cure the diseases, it is necessary to allow circadian rhythm to be balanced well by promoting smooth melatonin secretion in the evening time period by suppressing melatonin secretion in the morning time period.

Meanwhile, general illuminance measuring apparatuses measure illuminance Lux of external light using a visual lambda $V(\lambda)$ filter according to a photo sensing property curve, that is, a visual sensitivity curve with respect to human eyes. Here, the illuminance Lux means intensity of light capable of being recognized by human eyes and will be referred to as visual illuminance Lux hereinafter to be distinguished from bio illuminance Biolux which will be described.

According to the visual sensitivity curve, light having a wavelength band of 380 nm to 780 nm has a maximum sensitivity.

However, when a general illuminance measuring apparatus according to the visual sensitivity curve measures a visual illuminance value without correction with respect to different types of external light, a bio illuminance value having an effect on circadian rhythm of a human may vary according to a type of an external light source.

This is because an emission spectrum varies according to the type of the external light source, and a photo sensing property with respect to hormones which control circadian rhythm also varies when the emission spectrum varies.

For the same reason, in order to measure bio illuminance, it is important to detect a color temperature of the external light source or circadian action factor (CAF) information.

However, in order to obtain the above information, it is necessary to use an expensive reference spectrometer and there is a limitation in miniaturization due to properties of a sensor and a detector.

RELATED ART DOCUMENT

Patent Document

Korean Patent Publication No. 10-2001-0090519

SUMMARY OF THE INVENTION

The present invention is directed to providing an apparatus and a system for managing a circadian rhythm that is capable of measuring a circadian action factor and bio illuminance using a relatively simple method by applying a circadian lambda filter and a visual lambda filter thereto, miniaturizing a bio illuminance measuring apparatus by omitting an additional component for calculating the bio illuminance, and being applicable to a variety of products with a small cost.

The present invention is also directed to providing an apparatus and a system for managing a circadian rhythm that is capable of calculating an accurate bio illuminance value by calculating the bio illuminance value by reflecting a circadian action factor and a circadian action function which varies for each visual wavelength signal.

The present invention is also directed to providing an apparatus and a system for managing circadian rhythm that is capable of diagnosing circadian rhythm of a user by measuring bio illuminance and reinforcing the circadian rhythm of the user according to the diagnosed circadian rhythm of the user.

The present invention is also directed to providing an apparatus and a system for managing circadian rhythm that is capable of diagnosing circadian rhythm of a user in consideration of not only a bio illuminance value but also bio data and surrounding environment data of the user and reinforcing the circadian rhythm of the user.

The technical objectives of the present invention are not limited to the above technical objectives and additional unstated technical objectives will be clearly understood by one of ordinary skill in the art from the following description.

According to an aspect of the present invention, there is provided a circadian rhythm management apparatus including an illuminance measuring portion which measures a bio illuminance value of external light using a circadian lambda filter which passes the external light along according to a circadian rhythm sensitivity curve and a visual lambda filter which passes the external light along according to a visual sensitivity curve, a controller which outputs a control signal which reinforces a user's circadian rhythm on the basis of the bio illuminance value, and a circadian rhythm reinforcing portion which emits light of a circadian wavelength band toward the user according to the control signal.

The illuminance measuring portion may include a photo sensing portion that senses and converts the external light, which has passed through the circadian lambda filter, into a circadian wavelength signal and senses and converts the external light, which has passed through the visual lambda filter, into a visual wavelength signal.

The illuminance measuring portion may further include an illuminance calculating portion which calculates a ratio between the circadian wavelength signal and the visual wavelength signal, calculates a circadian action factor by applying the ratio between the circadian wavelength signal and the visual wavelength signal to a circadian action function which varies according to the visual wavelength signal, and calculates the bio illuminance value on the basis of the circadian action factor.

The illuminance calculating portion may include a function storage which stores a plurality of circadian action functions which vary according to each of certain sections of the visual wavelength signal.

The illuminance calculating portion may further include a function caller which calls a function corresponding to the visual wavelength signal among the plurality of circadian action functions stored in the function storage.

The circadian action function may be a function which defines a relation between the circadian action factor and the ratio between the circadian wavelength signal and the visual wavelength signal. Also, the ratio between the circadian wavelength signal and the visual wavelength signal may become an independent variable, and the circadian action factor may become a dependent variable.

The circadian action factor may be proportional to the ratio between the circadian wavelength signal and the visual wavelength signal.

The illuminance calculating portion may include a visual illuminance calculator which calculates a visual illuminance value of the external light on the basis of the visual wavelength signal.

The bio illuminance value may be calculated by multiplying the circadian action factor by the visual illuminance value.

The control signal may be a signal related to light intensity and light emitting time of the circadian wavelength band.

The circadian rhythm reinforcing portion may include a light source which outputs light of the circadian wavelength band and a light source driving portion which receives the control signal and drives the light source.

According to another aspect of the present invention, there is provided a circadian rhythm management system including the above-described circadian rhythm management apparatus and a server which receives and analyzes at least one of a bio illuminance value, bio data of a user, surrounding environment data of the user and generates a control signal by analyzing the same.

The system may further include a patch which is attached to a body of the user and measures and outputs the bio data of the user to the server.

The system may further include a sensor which is disposed near the user and measures and outputs the surrounding environment data of the user to the server.

The system may further include a user terminal which displays at least one of the bio illuminance value and a visual illuminance value, transmits the bio illuminance value to the server, and transmits the control signal generated by the server to the controller.

The bio data may include at least one of heart rate data, electrocardiogram data, and core temperature data, and the surrounding environment data may include at least one of temperature data and humidity data.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
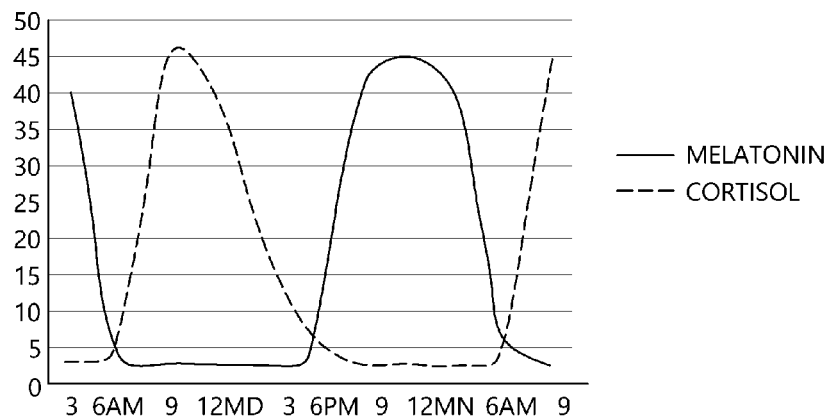
FIG. 1 is a graph illustrating melatonin and cortisol secretion rates according to a daily cycle of a human.

Exemplary embodiments according to the present invention will be described in detail with reference to the attached drawings. Regardless of signs in drawing, equal or similar elements will be referred to with like reference numerals and an overlapped description thereof will be omitted.

Also, in the description of the embodiments of the present invention, a detailed description of a well-known technology of the related art will be omitted when it is deemed to obscure the essence of the present invention. Also, it should be noted that the attached drawings are merely for allowing the concept of the present invention to be easily understood and the concept of the present invention is not to be construed as being limited to the attached drawings.

FIG. 1 is a graph illustrating melatonin and cortisol secretion rates according to a daily cycle of a human.

As shown in FIG. 1, it may be seen that a melatonin secretion rate is very low from 6 a.m. to 6 p.m., rapidly increases from 6 p.m., is at a maximum value at midnight, and is rapidly reduced until 6 a.m.

Also, it may be seen that a cortisol secretion rate is very low from 6 p.m. to 6 a.m., rapidly increases from 6 a.m., is at a maximum value at noon, and is rapidly reduced until 6 p.m.

As described above, a bio illuminance measuring apparatus according to an embodiment of the present invention measures a bio illuminance value Biolux using hormones such as melatonin and cortisol, which control circadian rhythm of a human as relating to light.

Figure 2:
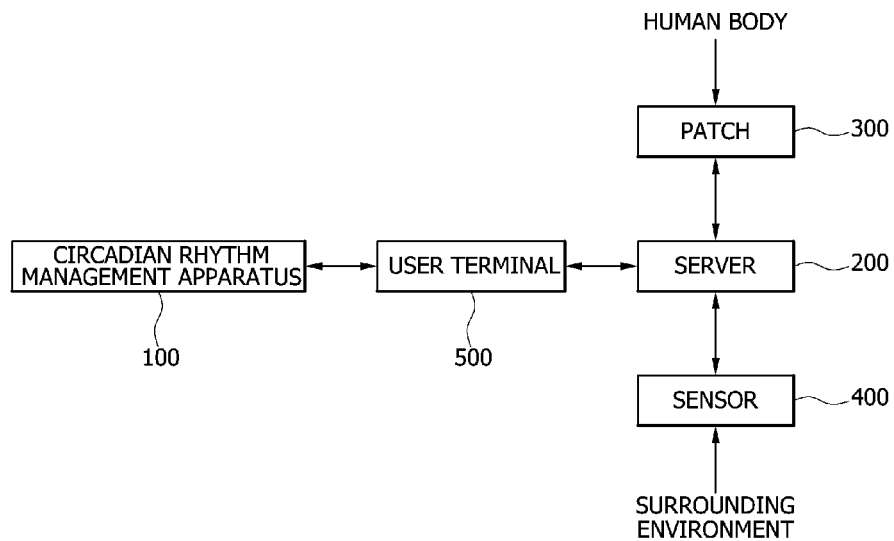
FIG. 2 is a schematic block diagram of a circadian rhythm management system according to an embodiment of the present invention.
Figure 3:
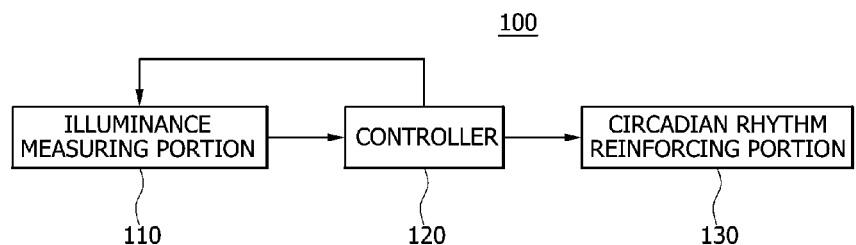
FIG. 3 is a schematic block diagram of a circadian rhythm management apparatus according to an embodiment of the present invention.
Figure 4:
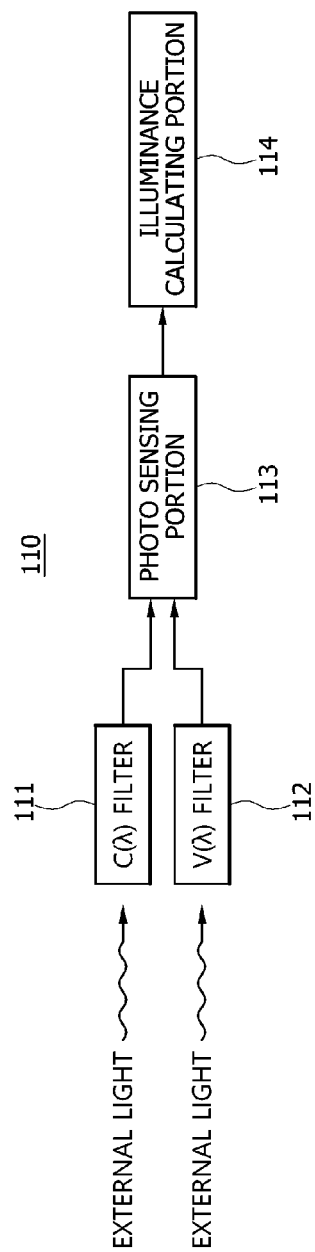
FIG. 4 is a schematic block diagram illustrating an illuminance measuring portion shown in FIG. 3.
Figure 5:
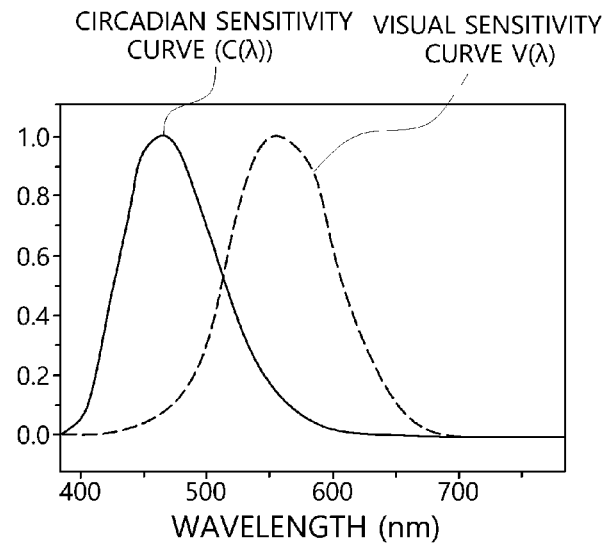
FIG. 5 is a graph illustrating a circadian rhythm sensitivity curve and a visual sensitivity curve.

FIG. 2 is a schematic block diagram of a circadian rhythm management system according to an embodiment of the present invention. Also, FIG. 3 is a schematic block diagram of a circadian rhythm management apparatus according to an embodiment of the present invention. FIG. 4 is a schematic block diagram illustrating an illuminance measuring portion shown in FIG. 3. FIG. 5 is a graph illustrating a circadian rhythm sensitivity curve and a visual sensitivity curve.

As shown in FIG. 2, the circadian rhythm management system according to the present invention may include a circadian rhythm management apparatus 100, a server 200, a patch 300, a sensor 400, and a user terminal 500.

These components may send and receive data through wired or wireless communications. That is, these components may include a communication portion (not shown), for example, a Bluetooth low energy (BLE) module, and may perform a function of wirelessly transmitting and receiving digital data and control signals through the communication portion.

As shown in FIG. 3, the circadian rhythm management apparatus 100 according to the embodiment of the present invention may include an illuminance measuring portion 110, a controller 120, and a circadian rhythm reinforcing portion 130.

The illuminance measuring portion 110 measures a bio-illuminance value Biolux of external light using a circadian lambda filter (C(λ) filter) 111 and a visual lambda filter (V(λ) filter) 112.

The controller 120 outputs a control signal for reinforcing a circadian rhythm of a user on the basis of the bio-illuminance value Biolux measured by the illuminance measuring portion 110.

The circadian reinforcing portion 130 receives the control signal input from the controller 120 and emits light of a circadian wavelength band toward user's eyes.

As shown in FIG. 4, the illuminance measuring portion 110 may include the circadian lambda filter 111, the visual lambda filter 112, a photo sensing portion 113, and an illuminance calculating portion 114.

The circadian lambda filter 111 passes external light along according to a circadian rhythm sensitivity curve.

As shown in FIG. 5, the circadian rhythm sensitivity curve is a photo sensing property curve with respect to hormones (for example, melatonin or cortisol) that control a circadian rhythm of a human and has a maximum sensitivity at a circadian wavelength band. Here, the circadian wavelength band may be 400 nm to 600 nm.

According to the circadian rhythm sensitivity curve, light having a wavelength band of 400 nm to 600 nm has a maximum sensitivity.

Accordingly, the circadian lambda filter 111 according to the circadian rhythm sensitivity curve operates as a band pass filter which passes external light along that has a wavelength of 400 nm to 600 nm, which is the circadian wavelength band, and blocks external light having other wavelength bands.

Also, the circadian lambda filter 111 transmits light having a wavelength of 400 nm to 600 nm and has a maximum transmittance at a wavelength band of about 450 nm.

The visual lambda filter 112 passes external light along according to a visual sensitivity curve.

As shown in FIG. 5, the visual sensitivity curve is a photo sensing property curve with respect to human eyes and is a curve having a maximum sensitivity at a visual wavelength band. Here, the visual wavelength band may be 380 nm to 780 nm.

According to the visual sensitivity curve, light having a wavelength band of 380 nm to 780 nm has a maximum sensitivity.

Accordingly, the visual lambda filter 112 according to the visual sensitivity curve operates as a band pass filter which passes external light along that has a wavelength of 380 nm to 780 nm, which is the visual wavelength band, and blocks external light having other wavelength bands.

Figure 6:
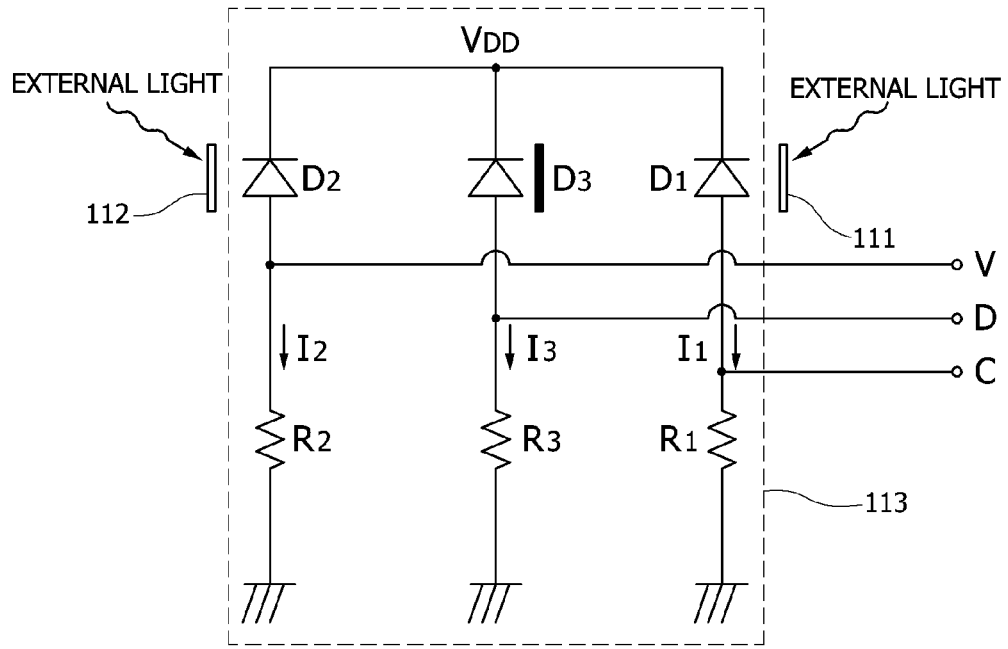
FIG. 6 is a detailed circuit diagram illustrating a photo sensing portion shown in FIG. 4.

FIG. 6 is a detailed circuit diagram illustrating the photo sensing portion shown in FIG. 4.

As shown in FIG. 6, the photo sensing portion 113 senses external light which has passed through the circadian lambda filter 111, converts the external light into a circadian wavelength signal C (for example, a voltage value), senses external light which has passed through the visual lambda filter 112, converts the external light into a visual wavelength signal V (for example, a voltage value), and outputs the visual wavelength signal V.

Here, the photo sensing portion 113 may include first to third photo diodes $D_1$ to $D_3$ and first to third variable resistors $R_1$ to $R_3$ and may output values corresponding to values obtained by integrating amounts of light passing through each of the circadian lambda filter 111 and the visual lambda filter 112 for each wavelength.

Here, the first photo diode $D_1$ and the first variable resistor $R_1$ are connected in series and form a first circuit, the second photo diode $D_2$ and the second variable resistor $R_2$ are connected in series and form a second circuit, and the third photo diode $D_3$ and the third variable resistor $R_3$ are connected in series and form a third circuit. Also, the first to third circuits are connected in parallel.

In detail, the first photo diode $D_1$ senses external light which has passed through the circadian lambda filter 111 and outputs a circadian wavelength current $I_1$ corresponding thereto, the second photo diode $D_2$ senses external light which has passed through the visual lambda filter 112 and outputs a visual wavelength current $I_2$ corresponding thereto, and the third photo diode $D_3$ outputs a dark current $I_3$ in a dark state in which external light is blocked.

Also, the first variable resistor $R_1$ converts the circadian wavelength current $I_1$ output from the first photo diode $D_1$ into a circadian wavelength voltage VC, the second variable resistor $R_2$ converts the visual wavelength current $I_2$ output from the second photo diode $D_2$ into a visual wavelength voltage VV, and the third variable resistor $R_3$ converts the dark current $I_3$ output from the third photo diode $D_3$ into a dark voltage VD.

That is, a voltage applied to both ends of the first variable resistor $R_1$ becomes the circadian wavelength voltage VC, a voltage applied to both ends of the second variable resistor $R_2$ becomes the visual wavelength voltage VV, and a voltage applied to both ends of the variable resistor $R_3$ becomes the dark voltage VD.

Here, the circadian wavelength signal C is a first analog signal corresponding to a difference between the circadian wavelength voltage VC and the dark voltage VD, and the visual wavelength signal V is a second analog signal corresponding to a difference between the visual wavelength voltage V and the dark voltage D.

That is, the circadian wavelength signal C may be defined by the following Equation 1, and the visual wavelength signal V may be defined by the following Equation 2.

$$C=(I_1 \times R_1)-(I_3 \times R_3)=VC-VD \quad \text{[Equation 1]}$$

$$V=(I_2 \times R_2)-(I_3 \times R_3)=VV-VD \quad \text{[Equation 2]}$$

As described above, the photo sensing portion 113 according to the embodiment of the present invention may remove self-generated noise inherent in a photo diode by calculating the circadian wavelength signal C and the visual wavelength signal V as differential voltages obtained by deducting the dark voltages VD from the circadian wavelength voltage VC and visual wavelength voltage VV so as to precisely sense the circadian wavelength signal C and the visual wavelength signal V therethrough.

Figure 7:
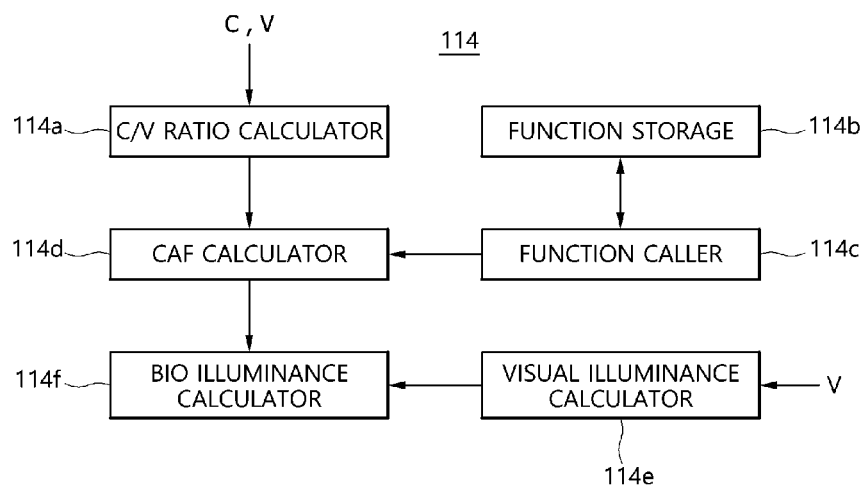
FIG. 7 is a detailed block diagram illustrating an illuminance calculating portion shown in FIG. 4.

FIG. 7 is a detailed block diagram illustrating the illuminance calculating portion shown in FIG. 4.

As shown in FIG. 7, the illuminance calculating portion 114 may include a C/V ratio calculator 114a, a function storage 114b, a function caller 114c, a circadian action factor (CAF) calculator 114d, a visual illuminance calculator 114e, and a bio illuminance calculator 114f.

The illuminance calculating portion 114 may receive the circadian wavelength signal C and the visual wavelength signal V, which are analog signals output by the photo sensing portion 113, that is, the first analog signal and the second analog signal, and convert the circadian wavelength signal C and the visual wavelength signal V into digital signals.

The C/V ratio calculator 114a receives the circadian wavelength signal C and the visual wavelength signal V from the photo sensing portion 113 and calculates a ratio (C/V ratio) between the circadian wavelength signal C and the visual wavelength signal V.

The CAF calculator 114d calculates a CAF on the basis of the ratio (C/V ratio) between the circadian wavelength signal C and the visual wavelength signal V.

Here, the CAF may be defined as a ratio of circadian efficacy of radiation (CER) with respect to luminous efficacy of radiation (LER).

Figure 8:
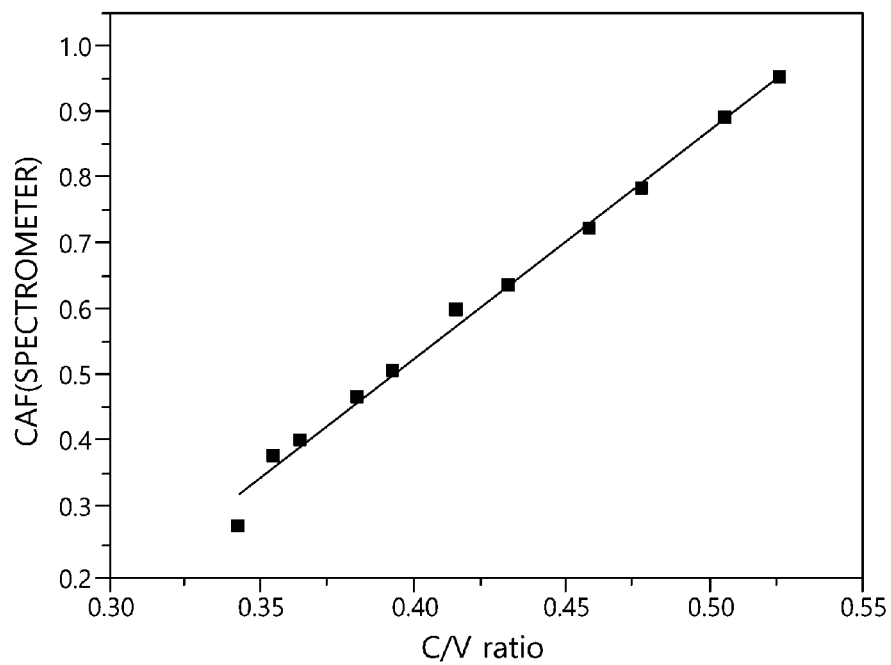
FIG. 8 is a graph illustrating a relation between a reference circadian action function (CAF) and a C/V ratio.

FIG. 8 is a graph illustrating a relation between a reference CAF and a C/V ratio.

Here, the reference CAF was measured using an additional reference spectrometer, and a ratio (C/V ratio) of a circadian wavelength signal C to a visual wavelength signal V was measured by the C/V ratio calculator 114a of the present invention.

As shown in FIG. 8, it may be seen that the ratio (C/V ratio) of the circadian wavelength signal C to the visual wavelength signal V is linearly proportional to the reference CAF.

Figure 9A:
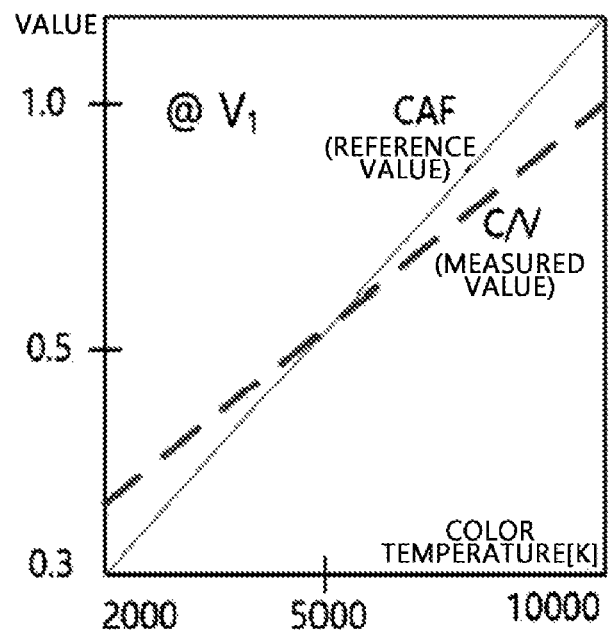
FIGS. 9A to 9C are graphs illustrating a relation between CAF and a C/V ratio, which varies according to a visual wavelength signal.
Figure 9B:
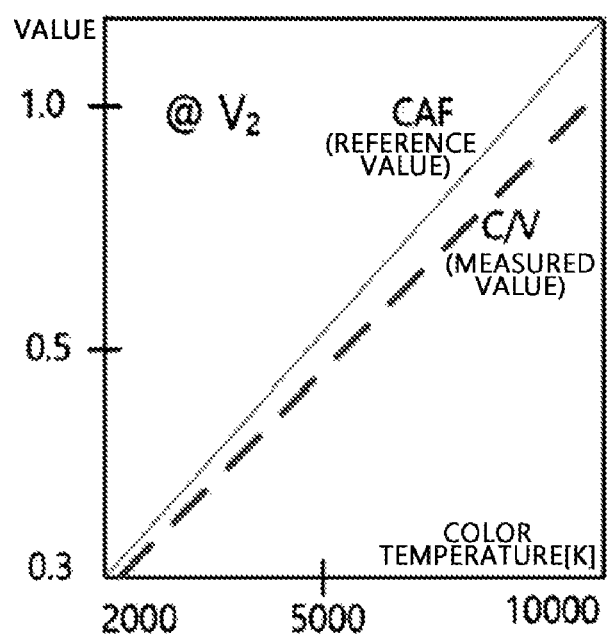
Figure 9C:
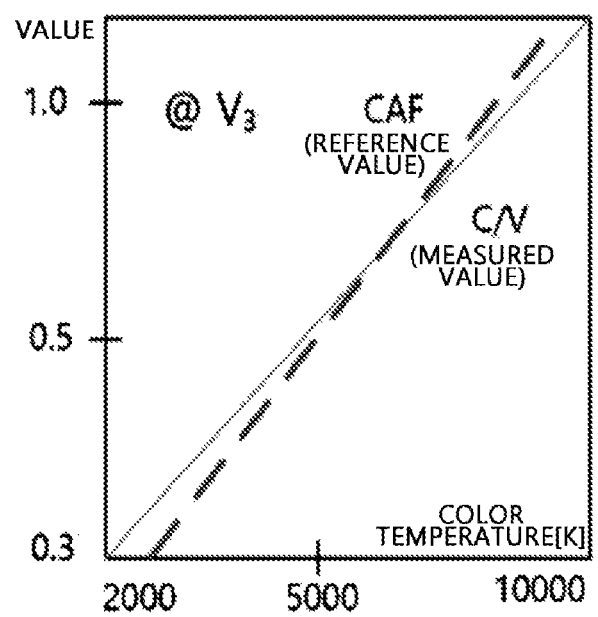

FIGS. 9A to 9C are graphs illustrating a relation between CAF and a C/V ratio, which varies according to a visual wavelength signal.

Here, the C/V ratio calculator 114a of the present invention calculates a ratio (C/V ratio) of a circadian wavelength signal C to a visual wavelength signal V with respect to external light having a different color temperature, and the ratio is shown for each color temperature in the graph. Also, an additional reference spectrometer (not shown) measured a reference CAF with respect to each of other types of external light which have different color temperatures, and the reference CAF shown in the drawings for each color temperature.

As shown in FIG. 9, it may be seen that the ratio (C/V ratio) of the circadian wavelength signal C to the visual wavelength signal V and the reference CAF are proportional to a color temperature of external light.

Also, it may be seen that a certain functional relation is present between the CAF and the ratio (C/V ratio) of the circadian wavelength signal C to the visual wavelength signal V. Also, the relation may be defined by the following Equation 3.

$$CAF=F(C/V \text{ ratio})=A \times (C/V \text{ ratio})+B \quad \text{[Equation 3]}$$

Here, F(C/V ratio) is a circadian action function, and A and B are certain constants and may vary according to a visual wavelength signal V. That is, referring to FIGS. 9A to 9C, the circadian action function F(C/V ratio) varies according to the visual wavelength signal V.

The circadian action function F(C/V ratio) is a function which defines the relation between the CAF and the ratio (C/V ratio) of the visual wavelength V to the circadian wavelength signal C, in which the ratio between the circadian wavelength signal C and the visual wavelength signal V is an independent variable and the CAF is a dependent variable.

Meanwhile, V1, V2, and V3 shown in FIGS. 9A to 9C may refer to representative values among visual wavelength signals V within a certain range. Here, the circadian action function F(C/V ratio) may vary for each certain range of the visual wavelength signal V.

The function storage 114b stores a plurality of circadian action functions F(C/V ratios) which vary for each certain range of the visual wavelength signal V.

The function caller 114c calls a function corresponding to the visual wavelength signal V input from the photo sensing portion 113 among the plurality of circadian action functions F(C/V ratios) stored in the function storage 114b.

The CAF calculator 114d calculates the CAF by applying the C/V ratio calculated by the C/V calculator 114a to the circadian action function F(C/V ratio) called by the function caller 114c.

The bio illuminance calculator 114f calculates a bio illuminance value Biolux of external light on the basis of the CAF.

Figure 10:
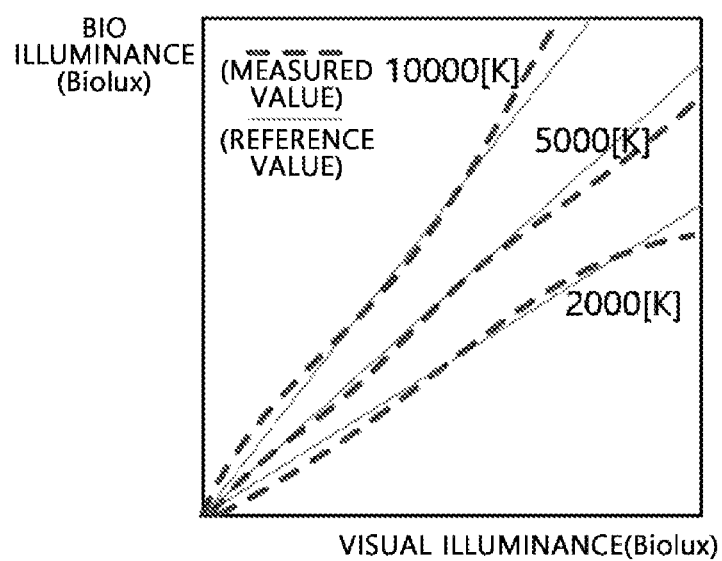
FIG. 10 is a graph illustrating a relation between visual illuminance and bio illuminance.

FIG. 10 is a graph illustrating a relation between visual illuminance and bio illuminance.

As shown in FIG. 10, visual illuminance Lux and bio illuminance Biolux are directly proportional to each other, and a proportional constant thereof is a CAF. Also, the relation between the visual illuminance Lux and bio illuminance Biolux varies according to a color temperature of external light, and the CAF is a function of the color temperature of the external light and increases as the color temperature increases.

Accordingly, the bio illuminance Biolux may be defined by the following Equation 4.

$$\text{Biolux}=\text{CAF} \times \text{Lux} \quad \text{[Equation 4]}$$

The illuminance calculating portion 114 may be divided into the visual illuminance calculator 114e and the bio illuminance calculator 114f.

Here, the visual illuminance calculator 114e receives the visual wavelength signal V and calculates a visual illuminance value Lux on the basis thereof, and the bio illuminance calculator 114f receives the CAF from the CAF calculator 114d and calculates a bio illuminance value Biolux of external light on the basis of the CAF.

In detail, the bio illuminance calculator 114f receives the visual illuminance value Lux from the visual illuminance calculator 114e and calculates the bio illuminance value Biolux by multiplying the visual illuminance value Lux by the CAF.

As described above, the illuminance measuring portion 110 according to the embodiment of the present invention may measure the bio illuminance value Biolux using a relatively simple method, in comparison to a conventional method, by directly calculating the CAF using the circadian lambda filter 111 and the visual lambda filter 112 and calculating the bio illuminance value Biolux on the basis thereof.

Also, since the bio illuminance value Biolux is calculated by reflecting the CAF and the circadian action function F(C/V ratio) which varies for each visual wavelength signal, it is possible to calculate a precise bio illuminance value Biolux.

Also, since it is possible to omit an additional component for calculating the bio illuminance value Biolux, a bio illuminance measuring apparatus may be miniaturized and is applicable to a variety of products at a low cost.

Figure 11:
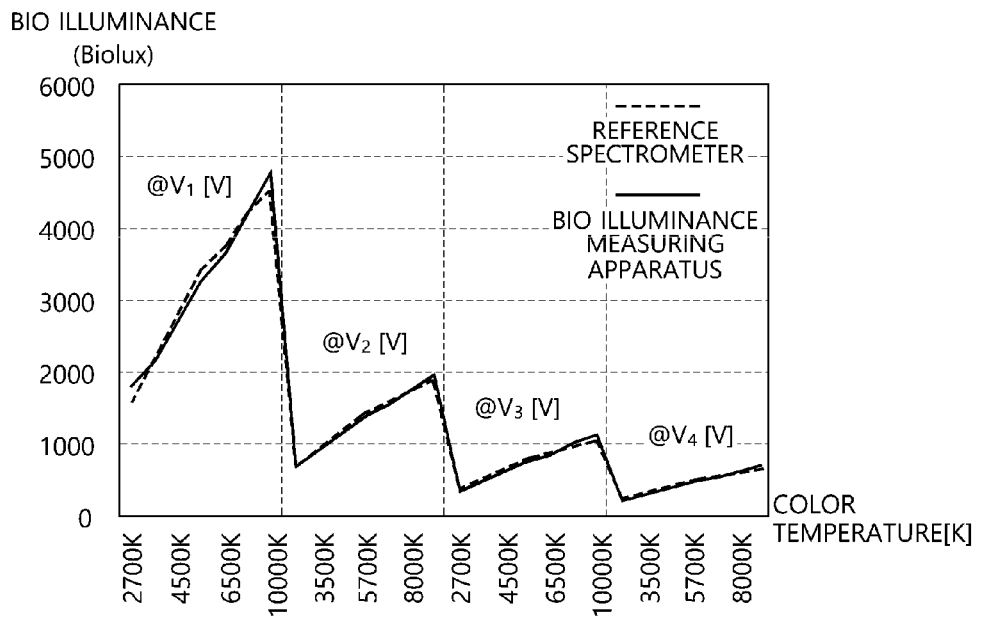
FIG. 11 is a graph illustrating a comparison between bio illuminance values measured by an illuminance measuring portion according to an embodiment of the present invention and a reference spectrometer.

FIG. 11 is a graph illustrating a comparison between bio illuminance values measured by the illuminance measuring portion and the reference spectrometer according to the embodiment of the present invention.

As shown in FIG. 11, it may be seen that the bio illuminance value Biolux measured by the illuminance measuring portion according to the embodiment of the present invention and the bio illuminance value Biolux measured by the reference spectrometer have approximately equal patterns. Also, it may be seen that a bio illuminance value Biolux increases in proportion to a color temperature of external light and has a different pattern according to a certain range of a visual wavelength signal V of the external light.

The controller 120 may adjust a voltage gain value with respect to external light by varying resistance values of the first to third variable resistors $R_1$ to $R_3$ of the photo sensing portion 113. That is, when digital signals obtained by conversion of the illuminance calculating portion 114 deviate from a processible range and become saturated, the controller 120 reduces the resistance values of the first to third variable resistors $R_1$ to $R_3$ by outputting a control signal to the photo sensing portion 113 such that the photo sensing portion 113 outputs a first analog signal C and a second analog signal V within a range processible by the illuminance calculating portion 114.

The controller 120 may output a control signal, which reinforces the circadian rhythm of the user on the basis of the bio-illuminance value Biolux measured by the illuminance measuring portion 110, to the circadian rhythm reinforcing portion 130.

Figure 12:
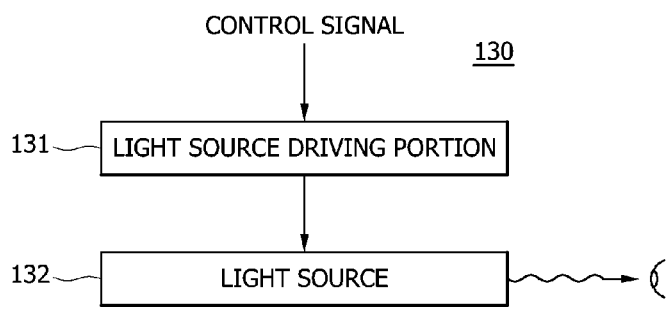
FIG. 12 is a detailed block diagram illustrating a circadian rhythm reinforcing portion shown in FIG. 3.

FIG. 12 is a detailed block diagram illustrating the circadian rhythm reinforcing portion shown in FIG. 3.

As shown in FIG. 12, the circadian rhythm reinforcing portion 130 according to the embodiment of the present invention may include a light source driving portion 131 and a light source 132 and emits light of a circadian wavelength band toward the user's eyes according to the control signal.

The light source driving portion 131 receives the control signal input from the controller 120 and drives the light source 132 such that the light source 132 outputs light of the circadian wavelength band and reinforces a user's circadian rhythm.

Here, the control signal may be a signal related to light intensity and light emitting time of the circadian wavelength band, and the light intensity and the light emitting time may be adjusted according to the measured bio illuminance value Biolux.

The circadian rhythm management apparatus 100 according to the embodiment of the present invention may diagnose the user's circadian rhythm by measuring the bio illuminance value Biolux using the illuminance measuring portion 110 and may reinforce the user's circadian rhythm using the circadian rhythm reinforcing portion 130 according to the user's diagnosed circadian rhythm.

That is, it is possible to correct user's distorted circadian rhythm by adjusting hormones which control circadian rhythm, and it is possible to cure diseases caused by a disturbance in circadian rhythm, for example, seasonal affective disorder, somnipathy, depression, fatigue caused by a time difference, and health conditions related to shift work.

For example, melatonin secretion of the user is suppressed by emitting light of a circadian wavelength band toward the user's eyes using the circadian rhythm reinforcing portion 130 in the morning time period such that the user's circadian rhythm may be well balanced by allowing melatonin secretion to be performed smoothly in the night time period.

As shown in FIG. 2, the server 200 may generate a control signal for reinforcing the user's circadian rhythm by receiving and analyzing at least one of the bio illuminance value Biolux, bio data of the user, and surrounding environment data of the user.

As described above, the control signal generated by the server 200 in consideration of not only the bio illuminance value Biolux but also the bio data and surrounding environment data of the user is input to the circadian rhythm reinforcing portion 130 such that the circadian rhythm reinforcing portion 130 may more effectively reinforce the user's circadian rhythm.

Also, the server 200 may accumulate, store, and update the bio illuminance value Biolux, the bio data of the user, and the surrounding environment data of the user.

The patch 300 may be attached to a user's body and may measure and output the bio data of the user to the server 200. The sensor 400 may be disposed near the user and may measure and output the surrounding environment data of the user to the server 200. Meanwhile, the sensor 400 may be manufactured in the form of a sticker and may be attached near the user.

Here, the bio data may include at least one of heart rate data, electrocardiogram data, and core body temperature data, and the surrounding environment data may include at least one of temperature data and humidity data.

The user terminal 500 may receive the bio illuminance value Biolux and the visual illuminance value Lux from the circadian rhythm management apparatus 100 and may display at least one of the bio illuminance value Biolux and the visual illuminance value Lux through a display portion (not shown).

Also, the user terminal 500 transmits the bio illuminance value Biolux to the server 200 and transmits the control signal generated by the server 200 to the controller 120.

Also, the user terminal 500 may store the user's circadian rhythm which varies according to a time flow, and an application which stores a reference bio illuminance value necessary according to the circadian rhythm may be loaded thereon.

Here, the reference bio illuminance value stored in the application and the measured bio illuminance value Biolux are compared. When the measured bio illuminance value Biolux is smaller than the reference bio illuminance value, a warning for reinforcing the circadian rhythm may be displayed on the display portion.

As a result, the user may be allowed to visually check a present circadian rhythm state of the user and to correct the circadian rhythm using the circadian rhythm reinforcing portion 130 according to the circadian rhythm state.

As described above, in the circadian rhythm management system according to the embodiment of the present invention, the illuminance measuring portion 110 may accurately measure bio illuminance Biolux, the server 200 may generate a user-customized circadian rhythm reinforcing control signal by processing the measured bio illuminance Biolux, bio data, and surrounding environment data as big data, and the light source 132 may emit light of a circadian wavelength band toward the user's eyes by controlling the circadian rhythm reinforcing portion 130 according to the control signal such that a user-customized circadian rhythm reinforcing treatment may be performed.

According to the embodiments of the present invention, there are effects of measuring a circadian action factor and bio illuminance using a relatively simple method by applying a circadian lambda filter and a visual lambda filter thereto, miniaturizing a bio illuminance measuring apparatus by omitting an additional component for calculating the bio illuminance, and being applicable to a variety of products at a low cost.

Also, according to the embodiments of the present invention, an accurate bio illuminance value may be calculated by calculating a bio illuminance value by reflecting a circadian action factor and a circadian action function which vary for each visual wavelength signal.

Also, according to the embodiments of the present invention, there are effects of diagnosing circadian rhythm of a user by measuring bio illuminance and reinforcing the circadian rhythm of the user according to diagnosed circadian rhythm of the user.

Also, according to the embodiments of the present invention, circadian rhythm of a user may be effectively reinforced by diagnosing the circadian rhythm of the user in consideration of not only a bio illuminance value but also bio data and surrounding environment data of the user.

The effects of the present invention are not limited to the above effects, and additional unstated effects will be clearly understood by one of ordinary skill in the art from the following description.

The embodiments described in the specification and the attached drawings are merely for describing parts of the technical concept of the present invention as an example. Accordingly, since the embodiments disclosed herein are not intended to limit but rather explain the technical concept of the present invention, it is apparent that the range of the technical concept of the present invention is not to be limited by the above embodiments. It should be construed that modified examples and detailed embodiments easily derived by one of ordinary skill in the art without departing from the range of the technical concept included in the specification and drawings of the present invention are included in the scope of the present invention.

What is claimed is:

1. A circadian rhythm management apparatus comprising:
an illuminance measuring portion which measures a bio illuminance value of external light using a circadian lambda filter which passes the external light along according to a circadian rhythm sensitivity curve and a visual lambda filter which passes the external light along according to a visual sensitivity curve;
a controller which outputs a control signal which reinforces a user's circadian rhythm on the basis of the bio illuminance value,
wherein the illuminance measuring portion comprises a photo sensor that senses and converts the external light, which has passed through the circadian lambda filter, into a circadian wavelength signal and senses and converts the external light, which has passed through the visual lambda filter, into a visual wavelength signal;
an illuminance calculator which calculates a ratio between the circadian wavelength signal and the visual wavelength signal, calculates a circadian action factor by applying a ratio between the circadian wavelength signal and the visual wavelength signal to a circadian action function which varies according to the visual wavelength signal, and calculates the bio illuminance value on the basis of the circadian action factor; and a function storage which stores a plurality of circadian action functions which vary according to each of certain sections of the visual wavelength signal.

2. The circadian rhythm management apparatus of claim 1, further comprising a circadian rhythm reinforcer which emits light of a circadian wavelength band toward a user according to the control signal.

3. The circadian rhythm management apparatus of claim 2, wherein the circadian rhythm reinforcer comprises:
a light source which outputs light of the circadian wavelength band; and
a light source driving portion which receives the control signal and drives the light source.

4. The circadian rhythm management apparatus of claim 1, wherein the illuminance calculator further comprises a function caller which calls a function corresponding to the visual wavelength signal among the plurality of circadian action functions stored in the function storage.

5. The circadian rhythm management apparatus of claim 1, wherein the circadian action function is a function which defines a relation between the circadian action factor and the ratio between the circadian wavelength signal and the visual wavelength signal, and
wherein the ratio between the circadian wavelength signal and the visual wavelength signal becomes an independent variable, and the circadian action factor becomes a dependent variable.

6. The circadian rhythm management apparatus of claim 1, wherein the circadian action factor is proportional to the ratio between the circadian wavelength signal and the visual wavelength signal.

7. The circadian rhythm management apparatus of claim 1, wherein the illuminance calculator comprises a visual illuminance calculator which calculates a visual illuminance value of the external light on the basis of the visual wavelength signal.

8. The circadian rhythm management apparatus of claim 7, wherein the bio illuminance value is calculated by multiplying the circadian action factor by the visual illuminance value.

9. The circadian rhythm management apparatus of claim 1, wherein the control signal is a signal related to light intensity and light emitting time of the circadian wavelength band.

10. A circadian rhythm management system comprising:
the circadian rhythm management apparatus of claim 1; and
a server which receives and analyzes at least one of a bio illuminance value, bio data of a user, surrounding environment data of the user and generates a control signal by analyzing the same.

11. The circadian rhythm management system of claim 10, further comprising a patch which is configured to be attached to a body of the user and measures and outputs the bio data of the user to the server.

12. The circadian rhythm management system of claim 10, further comprising a sensor which is configured to be disposed near the user and measures and outputs the surrounding environment data of the user to the server.

13. The circadian rhythm management system of claim 10, further comprising a user terminal which displays at least one of the bio illuminance value and a visual illuminance value, transmits the bio illuminance value to the server, and transmits the control signal generated by the server to a controller.

14. The circadian rhythm management system of claim 10, wherein the bio data comprises at least one of heart rate data, electrocardiogram data, and core body temperature data, and wherein the surrounding environment data comprises at least one of temperature data and humidity data.

\* \* \* \* \*